United States Patent [19]

Takeuchi et al.

[11] Patent Number: 4,794,646
[45] Date of Patent: Dec. 27, 1988

[54] CHARGED BEAM PATTERN DEFECT INSPECTION APPARATUS

[75] Inventors: Susumu Takeuchi; Koichi Moriizumi, both of Itami, Japan

[73] Assignee: Mitsubishi Denki Kabushiki Kaisha, Tokyo, Japan

[21] Appl. No.: 896,213

[22] Filed: Aug. 14, 1986

[30] Foreign Application Priority Data

Aug. 14, 1985 [JP] Japan ............................. 60-179012

[51] Int. Cl.$^4$ ......................... G06K 9/00; G06K 9/62
[52] U.S. Cl. ........................................... 382/8; 382/30; 250/306; 250/442.1; 250/396 R; 358/106
[58] Field of Search ............... 382/8, 10, 16, 19, 22, 382/23, 25, 30, 32, 33, 34; 358/101, 106, 107; 250/306, 307, 308, 309, 310, 311, 442.1, 396 R, 397, 548

[56] References Cited

U.S. PATENT DOCUMENTS

| | | | |
|---|---|---|---|
| 3,699,304 | 10/1972 | Baldwin, Jr. et al. | 250/306 |
| 3,813,545 | 5/1974 | Barnhart et al. | 250/306 |
| 4,115,802 | 9/1978 | Kramer et al. | 358/106 |
| 4,514,629 | 4/1985 | Smith et al. | 250/397 |
| 4,567,364 | 1/1986 | Kano et al. | 250/307 |
| 4,581,762 | 4/1986 | Lapidus et al. | 382/23 |
| 4,600,839 | 7/1986 | Ichihashi et al. | 250/397 |
| 4,644,172 | 2/1987 | Sandland et al. | 250/548 |
| 4,680,469 | 7/1987 | Nomura et al. | 250/306 |

OTHER PUBLICATIONS

Harris et al., "Automated Inspection of Wafer Patterns with Applications in Stepping, Projection and Direct-Write Lithography", *Solid State Technology*, Feb. 1984.

*Primary Examiner*—James J. Groody
*Assistant Examiner*—Michael D. Parker
*Attorney, Agent, or Firm*—Birch, Stewart, Kolasch and Birch

[57] ABSTRACT

A charged beam pattern defect inspection apparatus for inspecting pattern defects on materials such as masks or wafers comprising: a collecting charged beam irradiation apparatus including scanning deflection device for accelerating and focusing the scanning beam, and a detector for detecting phenomenon produced by incident particles such as reflected electrons, secondary electrons, cathodeluminescent light, X rays, or absorption currents; a scanning and synchronous signal generator for generating a scanning signal to be control the scanning deflection means and a synchronous signal to fed into an A/D converter; a two-dimensional video memory including an A/D converter and an address signal generator; a video signal operator for operating the video signal stored in the two-dimensional video memory; a stage driving apparatus for driving a stage for holding the material to be inspected, which includes a position detector for detecting the position of the stage; an auxiliary memory device for storing inspection data; and a control operation apparatus for controlling the scanning and synchronous signal generator, the two dimensional video memory, the video signal operator, the stage driving apparatus, and the auxiliary memory device, and for outputting the output of the video signal operator as the result of pattern defect inspection.

10 Claims, 6 Drawing Sheets

F I G .4.
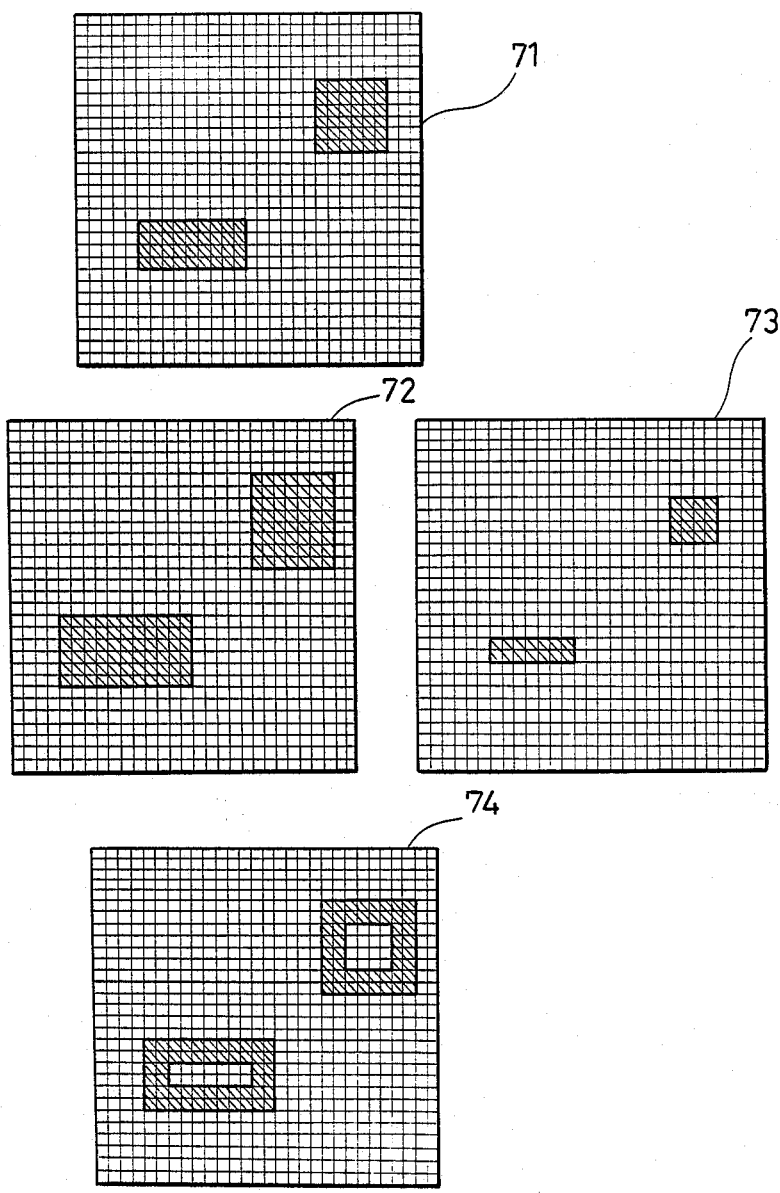

CHARGED BEAM PATTERN DEFECT INSPECTION APPARATUS

FIELD OF THE INVENTION

The present invention relates to a charged beam pattern defect inspection apparatus for inspecting pattern defects on materials such as a mask or wafer, and more particularly, for inspecting pattern defects of a miniaturized pattern on a mask or wafer.

BACKGROUND OF THE INVENTION

FIG. 5 shows a prior art pattern defect inspection apparatus. In FIG. 5, the numeral 21 designates a light source, numeral 22 designates an iris for producing an irradiation section of the light emitted from the light source 21, and numeral 23 designates a collecting lens for collecting the light. Numeral 24a designates a stage on which a material to be inspected 24 is mounted, and numeral 25 designates an image sensor which receives the light which has transpared the material 24. Reference numeral 14 designates a stage driving circuit for driving the stage 24a. Reference numeral 13 designates a video memory and video signal operator for storing the video signal obtained by the image sensor 25 and for executing a predetermined operation to the obtained video signal. Reference numeral 15 designates an auxiliary memory device for storing inspection data. Reference numeral 11 designates a control operation apparatus for controlling devices 13, 14, and 15 to obtain pattern defect information corresponding to the material 24.

The device operates as follows:

Light is emitted from the light source 21, reformed by the iris 22 to produce an irradiation section collected by the collecting lens 23, and irradiated onto the material to be inspected 24. The light which has transpared the material 24 has a brightness and darkness pattern in accordance with the pattern of the material 24. This light pattern is irradiated onto the image sensor 25. Thus, a video signal which has the intensity in proportional with the intensity of the light on each picture element is obtained by the image sensor 25. This video signal is stored in the video memory 13. The stored video data is processed using filtering, smoothing, and binarization performed by the video signal operator 13. A pattern data for inspection read out from the auxiliary memory device 15, and is stored into a separate video memory. The values of these two video memories are compared with each other to determine the pattern defects of the material. Then the positions of the defects on the material are calculated by taking into consideration the stage position and communicated to an operator.

In the pattern defect inspection apparatus using such a construction, although the edge of the obtained pattern is likely to fade to about the extent of the light wavelength, the preciseness of the pattern defect inspection is enhanced by the fact that signal processing is used to the obtained video signal. However, recently such an optical method in the pattern defect inspection has reached its limitation in preciseness. The limitation has been reached where the pattern is miniaturized and the width of the pattern is in the submicron region.

SUMMARY OF THE INVENTION

An object of the present invention is to provide a very precise pattern defect inspection apparatus which can also be used on a miniaturized pattern.

Other objects and advantages of the present invention will become apparent from the detailed description given hereinafter. It should be understood, however, that the detailed description and specific embodiment are given by way of illustration only, since various changes and modifications within the spirit and scope of the invention will become apparent to those skilled in the art from this detailed description.

The present invention is directed to a charged beam pattern defect inspection apparatus for inspecting pattern defects on materials such as masks or wafers comprising: a collecting charged beam irradiation apparatus including scanning deflection means for accelerating and focusing the scanning beam, and a detector for detecting phenomenon produced by incident particles such as reflected electrons, secondary electrons, cathodeluminescent light, X rays, or absorption currents; a scanning and synchronous signal generator for generating a scanning signal to control said scanning deflection means and a synchronous signal to be fed into an A/D converter described later; a two dimensional video memory including an A/D converter and an address signal generator; a video signal operator for operating a video signal stored in said video memory; a stage driving apparatus for driving a stage for holding the material to be inspected, which apparatus includes a position detector for detecting the position of the stage; an auxiliary memory device for storing inspection data; and a control operation apparatus for controlling said scanning and synchronous signal generator, said two dimensional video memory, said video signal operator, said stage driving apparatus, and said auxiliary memory device, and for outputting the output of said video signal operator as the result of pattern defect inspection.

BRIEF DESCRIPTION OF THE DRAWINGS

FIG. 4 is a diagram showing the process of obtaining the inspection data; and

DETAILED DESCRIPTION OF THE PREFERRED EMBODIMENTS

Figure 1:
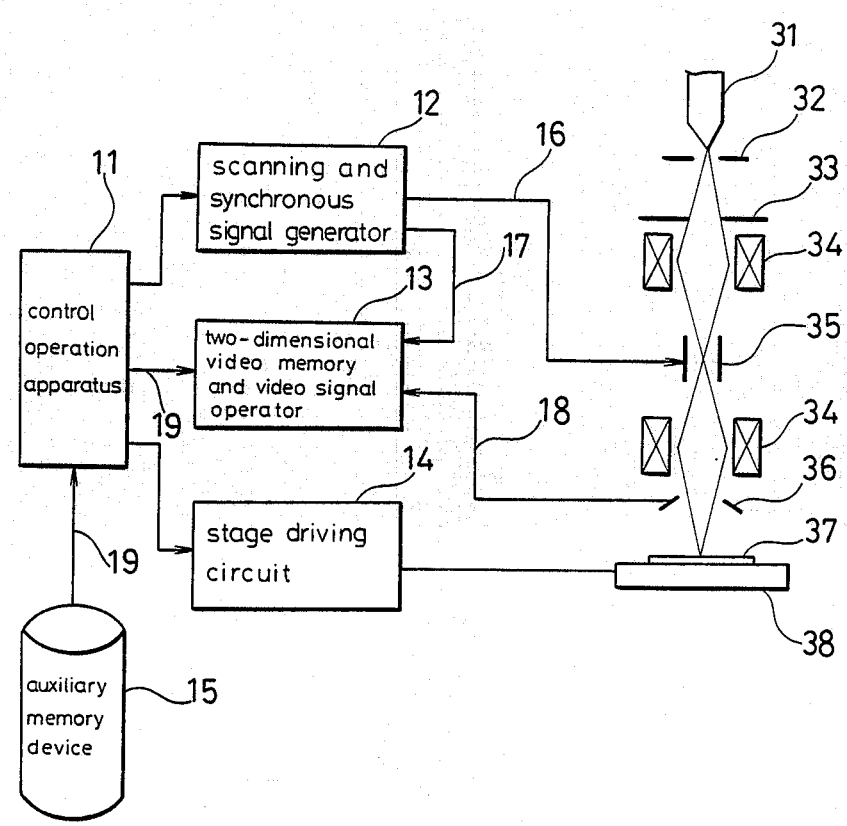
FIG. 1 is a diagram showing a charged beam pattern defect inspection apparatus as an embodiment of the present invention.

In order to explain the present invention in detail, reference will be particularly made to FIG. 1.

In FIG. 1, reference numeral 31 designates an electron beam gun, and numeral 32 designates an accelerating electrode for accelerating an electron beam emitted from the gun 31. Numeral 33 designates an aperture for producing an irradiation section from the accelerated electron beam, numeral 34 designates a collecting lens for collecting the electron beam, and numeral 35 designates a deflection electrode or coil for deflecting the electron beam. Reference numeral 36 designates a detector for detecting phenomenon produced by incident particles such as reflected electrons, secondary electrons, cathodeluminescent light, X rays, or absorption currents, numeral 37 designates the material to be inspected, and numeral 38 designates a stage for holding the material 37.

In FIG. 1, reference numeral 14 designates a stage driving circuit for driving the stage 38, and numeral 12 designates a scanning and synchronous signal generator for generating a scanning signal to control the scanning deflection coil 35 and a synchronous signal to be fed to a video memory described below. Numeral 13 designates a two dimensional video memory and video signal operator for storing the video signal obtained from the electron detector 36 and for executing a predetermined operation on the obtained video signal. Numeral 15 designates an auxiliary memory device for storing inspection data. Reference numeral 11 designates a control operation apparatus for controlling the devices 12, 13, 14, and 15 so as to obtain pattern defect information for the material 37. Besides, reference numeral 16 designates a scanning signal, numeral 17 designates a synchronous signal, numeral 18 designates a detected signal, and numeral 19 designates the flow of the inspection data.

Figure 2:
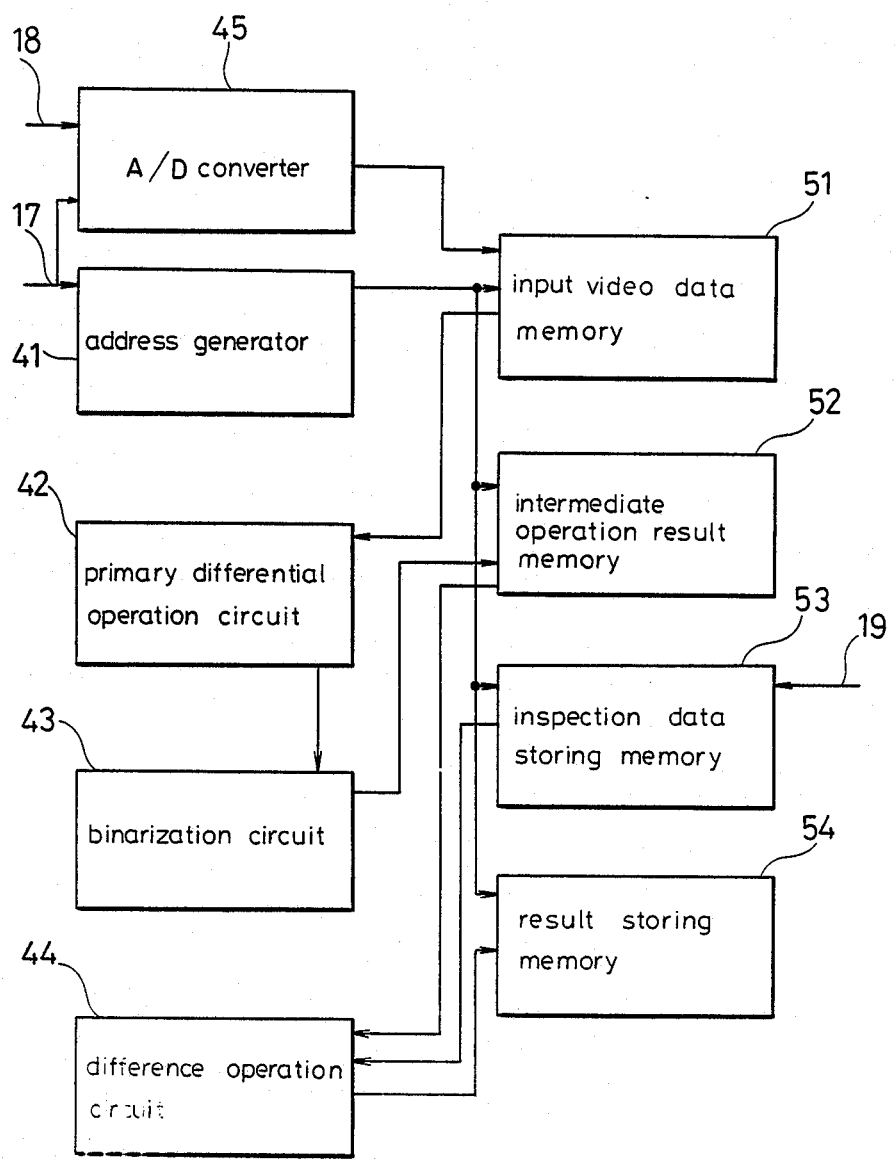
FIG. 2 is a diagram showing a two dimensional video memory and video signal operator of the embodiment.

FIG. 2 shows a construction of the two dimensional video memory and video signal operator 13. In FIG. 2, reference numeral 41 designates a memory address generator, numeral 42 designates a primary differential operation circuit, numeral 43 designates a binarization circuit, the numeral 44 designates a difference operation circuit, numeral 45 designates an A/D converter, the numeral 51 designates an input video data memory, numeral 52 designates an intermediate operation result memory, numeral 53 designates an inspection data storing memory, numeral 54 designates a result storing memory. Reference numerals 17, 18, and 19 designate the synchronous signal, the input video signal, and the inspection data similary as in FIG. 1.

The principle operation of the device will be described below.

In FIG. 1, electrons emitted from the electron beam gun 31 are accelerated by the accelerating electrode 32, and reformed by the aperture 33 to produce an irradiation section. The electrons which pass through the aperture 33 are collected by the collecting lens 34 and irradiated onto the material 37. Then, the scanning and synchronous signal generator 12 sends a scanning signal 16 to the deflection electrode 35, and a synchronous signal 17 to the two dimensional video memory and video signal operator 13.

The operation of the two dimensional video memory and video signal operator 13 will be described with reference to FIG. 2.

The address signal generator 41 generates an address for the input video data memory 51 from the synchronous signal 17 which is generated at the same time as the scanning signal 16 is generated. During the time frame, the input video signal 18 is converted into a digital signal with a quantization range of more than 4 bits by the A/D converter 45, and is stored at the address in the input video memory 51. After one frame of the video data from the input video memory 51 is read out, the address signal generator 41 generates a new address for the input video memory 51 and for writing in into the intermediate operation result memory 52. The primary differential operation circuit 42 reads out the data from the input video memory 51 by using the new address, and executes a primary differential operation on that data. The binarization circuit 43 compares the data from the primary differential operation circuit 42 with a predetermined threshold value to binarize the data, and the binarized data is written into the intermediate operation result memory 52 by using the above-mentioned address.

During the processes of converting the video data into a digital signal, and the differentiating and binarization of the data, the inspection data is read from the auxiliary memory device 15 shown in FIG. 1 and transferred to the inspection data storing memory 53 shown in FIG. 2 along path 19. After the conversion, differentiating and binarization of the data, and the storing of the inspection data are completed, the difference operation circuit 44 shown in FIG. 2 subtracts the content of the inspection data storing memory 53 from the content of the intermediate operation result memory 52, and stores the result of the subtraction in the memory 51. The address signals needed for read and write operations for this memory are generated by the address generator 41 similarly as described above.

Figure 3:
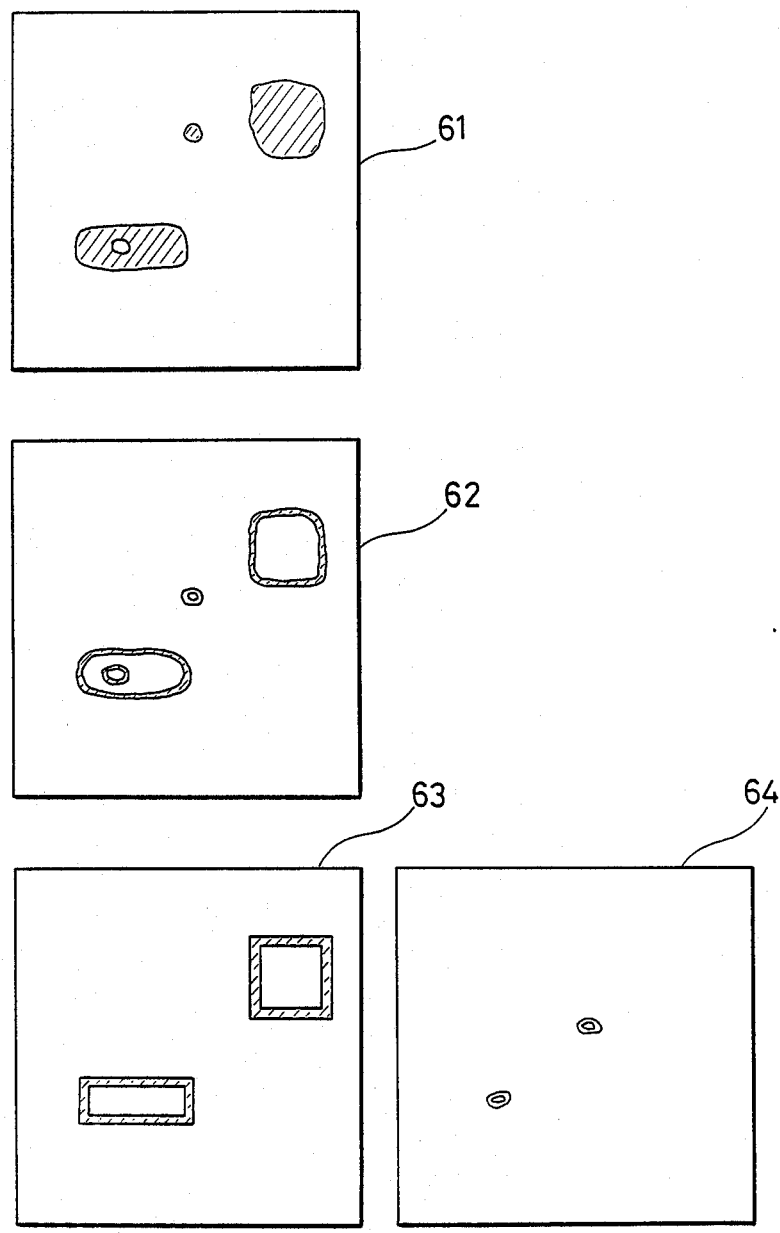
FIG. 3 is a diagram showing the change in the picture pattern for exemplifing the pattern defect inspection method of the embodiment.
Figure 5:
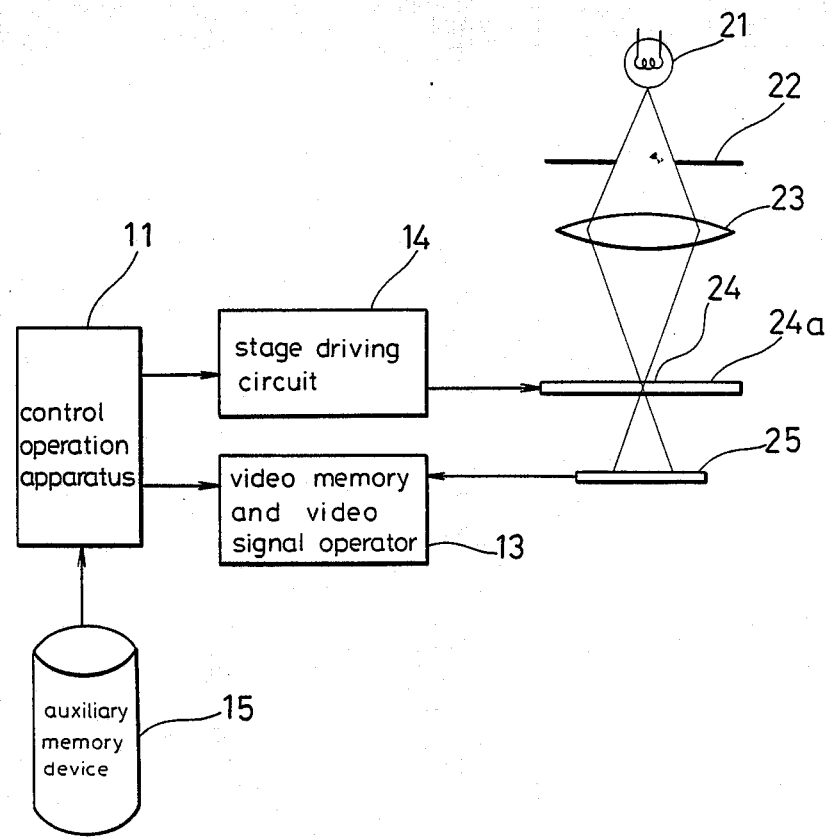
FIG. 5 is a diagram showing a prior art pattern defect inspection apparatus.

FIG. 3 shows a pattern in the video memory. Reference numeral 61 designates an input video signal. This input video signal has a range of a plurality of stages having a step of the quantization unit of the A/D converter 45. For example, in a case where an 8 bit A/D converter is used, the data has an intensity of an arbitrary value of 256 stages. Reference numeral 62 designates a pattern which is obtained after executing the primary differential operation and binarization on this input video signal. This pattern 62 is obtained by extracting the edge portion of the data of the pattern 61 and representing it by "0" or "1". Pattern 63 as shown in FIG. 3 is the inspection data stored in the inspection data storing memory 53 of FIG. 2. This data also represents binary data of ones and zeroes. This inspection data 63 is obtained from the design data that produced the pattern on a mask or wafer. This pattern is obtained by widening the width of the contour of the figure of the design data by 2 to 3 picture elements on the both sides. This pattern may be obtained by previous calculation of the contour of the figure of the design data to be stored in the auxiliary memory device as inspection data. This pattern may be also obtained by extending the figure of the design data into a separate two-dimensional memory, expanding this by about 1 to 2 picture element(s) and storing the same in an operation memory, compressing the original figure by about 1 to 2 picture element(s), and subtracting the compressed data from the expanded data. This process of obtaining inspection data is shown in FIG. 4. In FIG. 4, reference numeral 71 designates a pattern obtained by extending the design data, numeral 72 designates a pattern obtained by expanding the figure of the pattern 71 by 1 picture element, numeral 73 designates a pattern obtained by compressing the figure of the pattern 71 by 1 picture element, and numeral 74 designates the inspection pattern obtained by subtracting the pattern 73 from the pattern 72.

The inspection data 74 of FIG. 4 can be produced by processing the original design data 71 using software or hardware. An example of this process is shown in FIG. 6.

Figure 6:
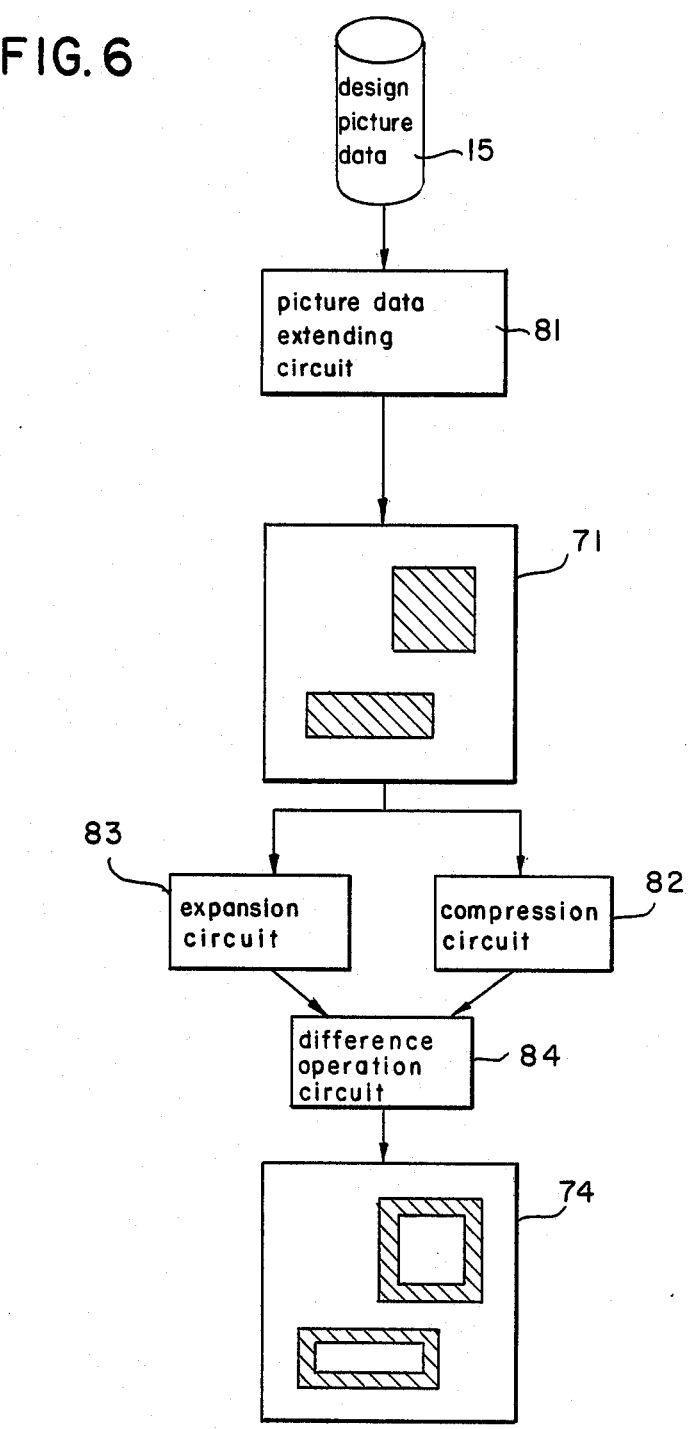

In FIG. 6, reference numeral 15 designates an auxiliary recording material which stores design picture data (this corresponds to to 15 of FIG. 1). Reference numeral 81 designates a picture data extending circuit for bit map extending of the design data and storing the extended design data in a two-dimensional array. The video image in the array can be seen by projection 71 (this corresponds to 71 of FIG. 4). This video image is read from the array by scanning and transferred to the compression circuit 82 and the expansion circuit 83. The output of the compression circuit is subtracted from the output of the expansion circuit by using the difference operation circuit 84, and the result is then stored in a separate two-dimensional array. The stored result is the inspection data as seen in projection 74.

A pattern 64 shown in FIG. 3 is pattern defect data which is obtained by subtracting the inspection data 63 from the pattern 62 obtained by the primary differential operation and the binarization, and this is stored in the result storing memory 54 of FIG. 2. This pattern defect data 64 have a value "1" only at the positions where a pattern defect exists, and these positions are communicated to the operator.

In this embodiment with such a construction, a collecting charged beam apparatus is used to obtain a video signal containing the pattern defect information of the material. The video signal is then processed by a primary differential operation and binarization operation performed by the video memory and the video signal operator. This processed signal then is compared with the inspection data to obtain the pattern defect information. This enables the pattern defect inspection to be performed with high precision and at a high speed even when the pattern width is miniaturized.

In the illustrated embodiment, an electron beam gun is used as a light source. However, an ion beam gun can also be effectively used.

In the illustrated embodiment, the quantization range of the A/D converter is 8 bits, but a quantization range of more than 4 bits can be used with the same effects.

What is claimed is:

1. A charged beam pattern defect inspection apparatus for inspection and determination of pattern defects on materials such as masks or wafers comprising:
   a collecting charged beam irradiation apparatus including,
     scanning beam source means, for producing a scanning beam,
     scanning deflection means, for accelerating and focusing the scanning beam, and
     a detector for detecting phenomenon produced by incident particles such as reflected electrons, secondary electrons, cathodeluminescent light, X rays, or absorption currents;
   a two dimensional video memory having,
     an A/D converter,
     a memory for storing a video signal, and
     an address signal generator;
   a scanning generator for generating a scanning signal to control said scanning deflection means;
   a synchronous signal generator for generating a synchronous signal to be fed into said A/D converter;
   a video signal operator, for performing operations upon the video signal stored in said memory and for producing an output;
   a stage driving means, for driving a stage, the stage holding the material to be inspected, including a position detector for detecting the position of the stage;
   an auxilliary memory device for storing inspection data; and
   a control operation means, for controlling said scanning signal generator, said synchronous signal generator, said two dimensional video memory, said video signal operator, said stage driver means, and said auxiliary memory device, and for outputting the output of said video signal operator, the output is the determination of the pattern defect inspection.

2. The charged beam pattern defect inspection apparatus as claimed in claim 1, wherein said video signal operator comprises:
   primary differential operation means, for performing a primary differential operation upon the video signal and for producing primary differential data;
   binarization means, for comparing the primary differential data with a predetermined threshold value to binarize the primary differential data and for producing a binarized data; and
   difference operation means, for obtaining a difference between the binarized data and the inspection data stored in said auxiliary memory device.

3. The charged beam pattern defect inspection apparatus as claimed in claim 1, wherein said A/D converter has a quantization range of more than 4 bits and said two dimensional video memory and said video signal operator has a bit depth equal to the quantization range of said A/D converter.

4. The charged beam pattern defect inspection apparatus as claimed in claim 1 further comprises:
   inspection data means, for developing the inspection data stored in said auxiliary memory device from design data.

5. The charged beam pattern defect inspection apparatus as claimed in claim 4, wherein said inspection data means comprises:
   memory means, for storing the design data;
   picture data extending means, for bit map extending the design data and for storing the extended design data in a two dimensional array;
   expansion means, operatively connected to said picture data extending means, for expanding the extended design data;
   compression means, operatively connected to said picture data extending means, for compressing the extended design data; and
   difference means, operatively connected to said compression means and said expansion means, for subtracting the compressed design data from the expanded design data and for producing the inspection data therefrom.

6. A pattern defect inspection apparatus for inspecting and determining pattern defects on materials such as masks or wafers comprising:
   control means, for producing a deflection control signal, a video memory control signal and a stage control signal;
   scan beam source means, for producing a scan beam to scan the material to be inspected;
   deflection means, responsive to said control means, for accelerating and focusing the scanning beam in response to the deflection control signal;
   detector means, for detecting phenomenon produced by the scan beam reflected from the material to be inspected and for producing a video signal in response to the detected phenomenon;
   video memory means, operatively connected to said detection means and said control means, responsive to said control means, for digitizing the video signal and for storing the digital video signal in response to the video memory control signal;

operator means, operatively connected to said video memory means, for performing operations upon the digital video signal and for producing a result;

stage means, responsive to said control means, for holding the material to be inspected and for moving the material to a desired position in response to the stage control signal; and inspection data memory means, for storing inspection data;

said control means outputs the result of the operator means, the result is the determination of the pattern defect inspection.

7. The charged beam pattern defect inspection device as claimed in claim 6, wherein said operator mean comprises:

primary differential operation means, for performing a primary differential operation upon the video signal and for producing primary differential data;

binarization means, for comparing the primary differential data with a predetermined threshold value to binarize the primary differential data and for producing a binarized data; and difference operation means, for obtaining a difference between the binarized data and the inspection data stored in said inspection data memory means.

8. The charged beam pattern defect inspection device as claimed in claim 6, wherein said video memory means comprises:

an A/D converter having a quantization range of more than 4 bits.

9. The charged beam pattern defect inspection device as claimed in claim 6 further comprises:

inspection data means, for developing the inspection data stored in said inspection data memory means from design data.

10. The charged beam pattern defect inspection device as claimed in claim 9, wherein said inspection data means comprises:

memory means, for storing the design data;

picture data extending means, for bit map extending the design data and for storing the extended design data in a two dimensional array;

expansion means, operatively connected to said picture extending means, for expanding the extended design data;

compression means, operatively connected to said picture data extending means, for compressing the extended design data; and difference means, operatively connected to said compression means and said expansion means, for substracting the compressed design data from the expanded design data and for producing the inspection data therefrom.

* * * * *